United States Patent [19]

Kobayashi

[11] Patent Number: 4,665,923
[45] Date of Patent: May 19, 1987

[54] NON-CONTACT TYPE TONOMETER

[75] Inventor: Katsuhiko Kobayashi, Tokyo, Japan

[73] Assignee: Tokyo Kogaku Kikai Kabushiki Kaisha, Tokyo, Japan

[21] Appl. No.: 801,960

[22] Filed: Nov. 26, 1985

[30] Foreign Application Priority Data

Nov. 27, 1984 [JP] Japan ................ 59-248762
Mar. 25, 1985 [JP] Japan ................ 60-59994
Mar. 30, 1985 [JP] Japan ................ 60-68189

[51] Int. Cl.$^4$ .............................................. A61B 3/16
[52] U.S. Cl. ................................................ 128/648
[58] Field of Search ................ 128/645, 648, 748; 356/138, 150, 153; 73/380

[56] References Cited

U.S. PATENT DOCUMENTS

| | | | |
|---|---|---|---|
| 3,538,754 | 11/1970 | Grolman et al. | 128/648 |
| 3,585,849 | 6/1971 | Grolman | 128/648 |
| 3,756,073 | 9/1973 | Lavallee et al. | 128/648 |
| 3,832,890 | 9/1974 | Grolman et al. | 128/648 |
| 3,882,718 | 5/1975 | Kriebel | 128/648 |

*Primary Examiner*—Kyle L. Howell
*Assistant Examiner*—Angela D. Sykes
*Attorney, Agent, or Firm*—Finnegan, Henderson, Farabow, Garrett and Dunner

[57] ABSTRACT

A non-contact type tonometer for measuring intraocular pressure of a human eye. The tonometer includes a fluid ejection nozzle to eject a fluid toward a cornea of an eye to be tested and an alignment control apparatus. The alignment control apparatus comprises a pair of alignment control systems disposed in a manner as to intersect the respective optical axes at one point on the central axis of the fluid ejection nozzle and to be symmetrical about the central axis. The alignment optical systems each include an index projection optical system for projecting an index spot light toward the cornea and an index detection system for forming a virtual image of the index spot light produced by means of corneal specular reflection from the eye on an observation system as an index image through a part of an index projection optical system of the other alignment optical system. Alignment control between the eye to be tested and the fluid ejection nozzle is determined by confirming a superposed relation of the pair of index images formed on the observation system.

16 Claims, 23 Drawing Figures

NON-CONTACT TYPE TONOMETER

BACKGROUND OF THE INVENTION

1. Field of the Invention

This invention relates to a non-contact type tonometer in which a fluid for transfiguring a cornea is ejected toward the cornea in order to transfigure the cornea and the intraocular pressure is measured based on the transfiguration of the cornea, and more particularly to an improvement of an alignment control apparatus with respect to the cornea under test.

2. Description of the Related Art

Heretofore, a non-contact type tonometer is known as disclosed in, for example, a U.S. Pat. No. 3,756,073. This conventional non-contact type tonometer utilizes an air pulse as a fluid for transfiguring the cornea. The conventional non-contact type tonometer includes a fluid ejecting nozzle adapted to eject the air pulse. The axis of the fluid ejecting nozzle is arranged so as to be in alignment with an optical axis of an observation optical system for observing the cornea. When the optical axis and the corneal axis connecting the corneal vertex to the center of curvature of the cornea are brought into alignment with respect to each other, and the distance from the center of curvature of the cornea to the tip portion of the fluid ejecting nozzle is set to be in a predetermined distance, the fluid ejecting nozzle ejects the air pulse toward the cornea under test. The cornea under test is pressurized and transfigured flat by the air pulse. The deformation under pressure of the cornea is detected by monitoring system including a light transmitter adapted to project a collimated beam of light onto the cornea and a telescopic receiver adapted to receive a reflection light from the cornea. The non-contact type tonometer is such designed so as to measure the intraocular pressure based on a predetermined quantity of deformation of the cornea.

The related art disclosed in U.S. Pat. No. 3,756,073 includes an alignment verification system adapted to verify the alignment between the corneal axis and the optical axis of an observation optical system and also to verify the distance (hereinafter referred to "working distance") from the center of curvature of the cornea to the tip portion of the fluid ejecting nozzle. The alignment verification system for the conventional non-contact tonometer includes a target projection system adapted to project an image of the target toward the cornea. The alignment verification system disclosed in the U.S. Pat. No. 3,756,073 uses an objective lens of the observation optical system as the target projection system. In the alignment verification system, the light from the target is projected in such a manner as to form an image in the center of the curvature of the cornea through the objective lens, and reflected light due to specular reflection of the cornea is returned again to the observation optical system through the objective lens in order to reimage a target image on the aiming reticle. According to the conventional non-contact type tonometer, the alignment with respect to the cornea is effected according to the sharpness and the position of the target image on the aiming reticle.

However, the conventional alignment verification system has a problem that alignment with respect to the cornea can not be effected correctly, since only one target image is formed on the aiming reticle which makes it difficult to examine the sharpness of the image and the position thereof on the aiming reticle. Furthermore, the related art has such a disadvantage as that since the light from the target is projected in order to form the target image in the center of curvature of the cornea, the working distance is obliged to depend on the radius of curvature of the cornea of the eye under test. Thus, measuring errors are often resulted.

OBJECTS AND SUMMARY OF THE INVENTION

It is therefore an object of the present invention to provide a non-contact type tonometer wherein a correct working distance can be obtained without depending on the radius of curvature of the cornea of the eye under test.

Another object of the present invention is to provide a non-contact type tonometer wherein an index projection optical system and a corneal transfiguration monitoring system adapted to detect the corneal transfiguration can be served for a double purpose.

For achieving the aforementioned objects, the non-contact type tonometer according to the present invention includes a pair of alignment optical systems disposed opposite to an eye to be tested in symmetrical positions with respect to an optical axis of an observation optical system, each of the alignment optical systems comprises an index projection optical system adapted to project an index light to a cornea in the form of parallel bundle of rays, and an index detecting system adapted to form a virtual image of the index light produced due to specular reflection of the cornea of the eye under test to an observation means through the index projection optical system of the other alignment optical system as an index image, and an alignment verification means between the eye under test and a nozzle for confirming a superposed relation of the pair of index images formed on the observation means.

BRIEF DESCRIPTION OF THE DRAWINGS

FIGS. 1 through 6 illustrate a non-contact type tonometer according to a first embodiment of the present invention, wherein:

FIGS. 7 and 8 illustrate a non-contact type tonometer according to a second embodiment of the present invention, wherein:

FIGS. 9 through 18 illustrate a non-contact type tonometer according to a third embodiment of the present invention, wherein:

FIGS. 19 through 23 illustrate a non-contact type tonometer according to a fourth embodiment of the present invention, wherein:

DETAILED DESCRIPTION OF THE PREFERRED EMBODIMENTS

A preferred embodiment of an alignment adjustment apparatus of a non-contact type tonometer according to the present invention will be described hereinunder with reference to the accompanying drawings.

Figure 1:
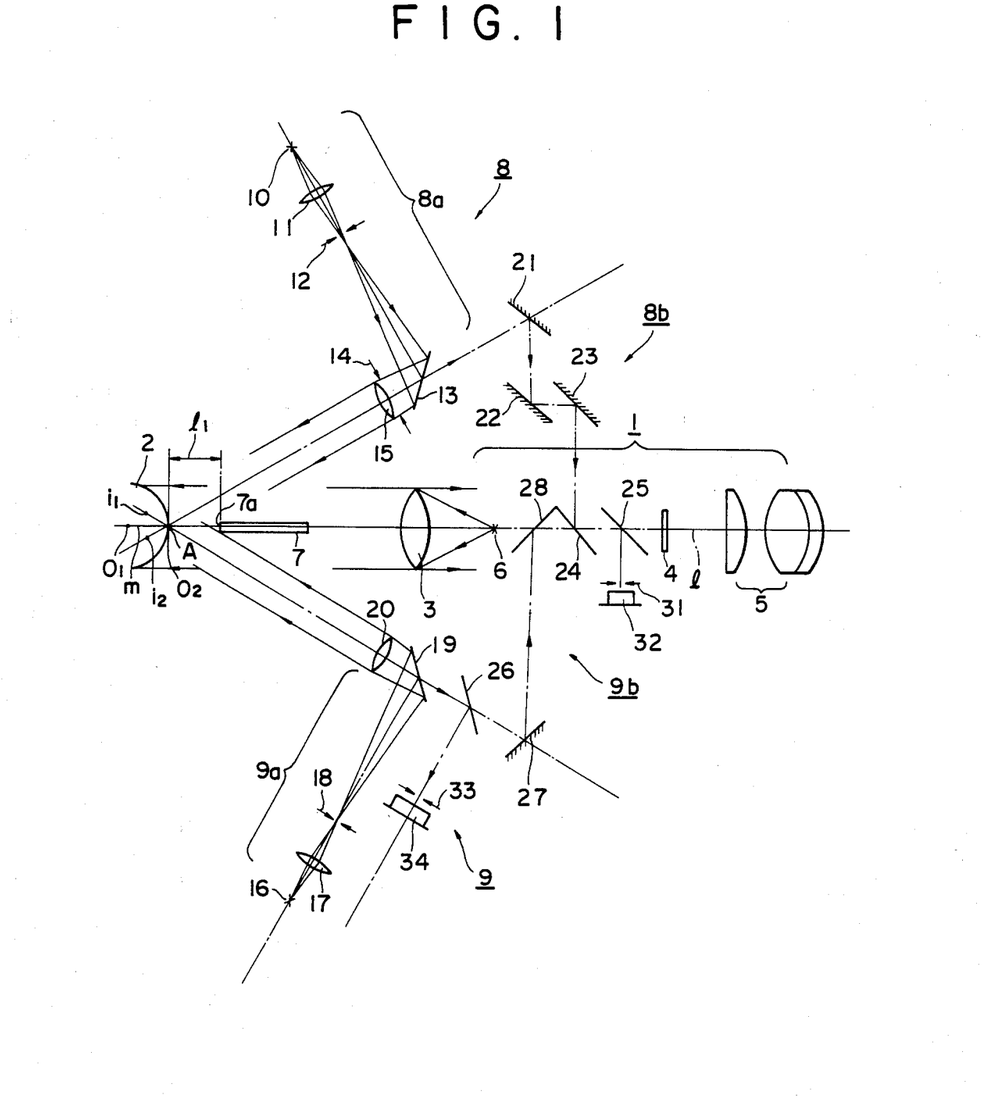
FIG. 1 is an optical system diagram showing the construction of a non-contact type tonometer according to the present invention.
Figure 2:
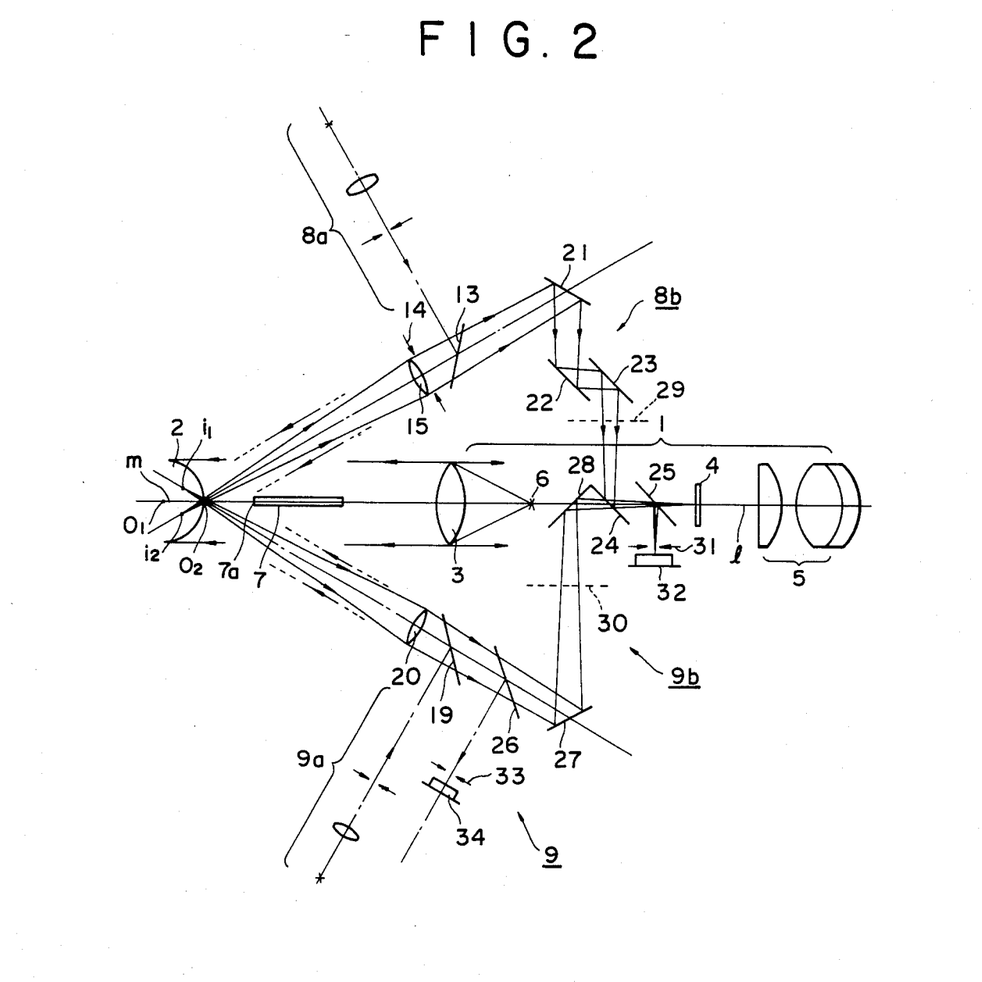
FIG. 2 is an optical system diagram showing a reflection light flux at a time when the alignment of a non-contact type tonometer according to the present invention is adjusted.
Figure 3:
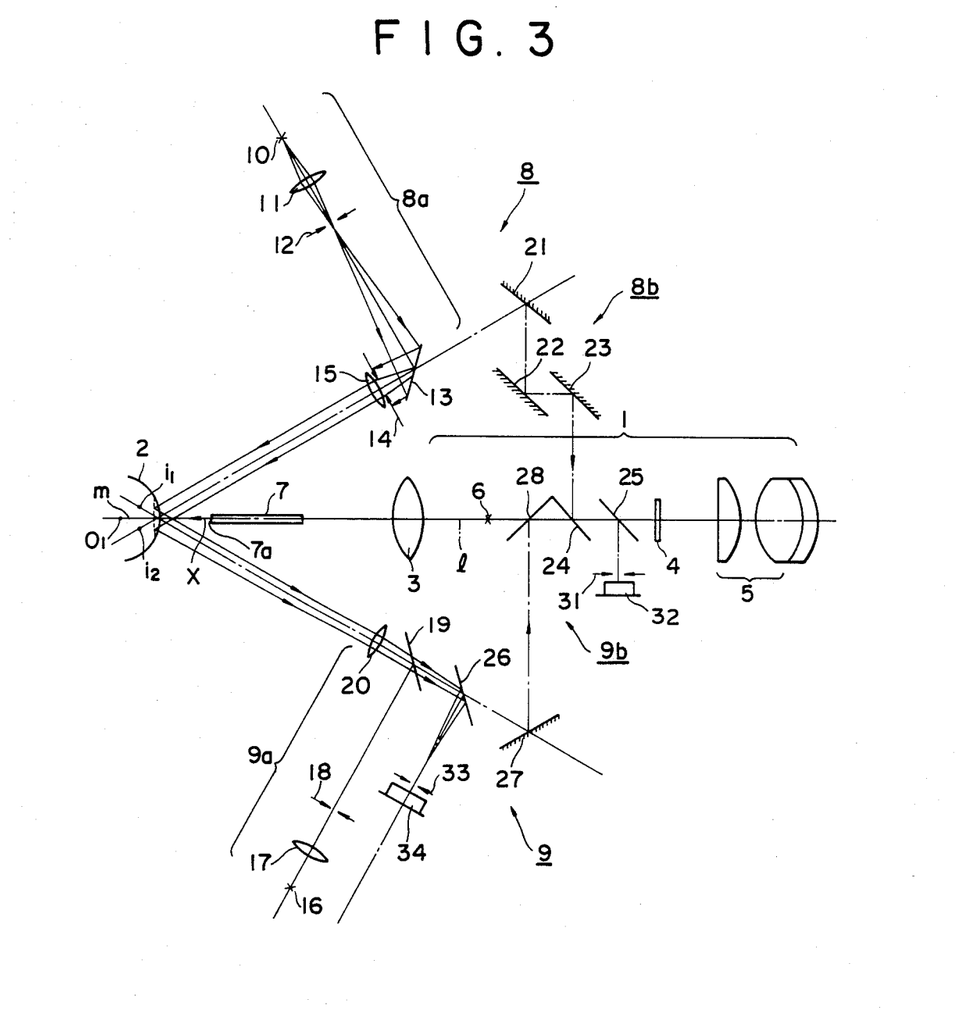
FIG. 3 is an optical system diagram for explaining a detection optical path of a non-contact type tonometer according to the present invention at a time when a cornea is transfigured.

FIGS. 1 through 6 illustrate a first embodiment of a non-contact type tonometer according to the present invention. In FIGS. 1 and 2, reference numeral 1 denotes an observation optical system, l denotes an optical axis thereof. Reference numeral 2 denotes a cornea of an eye to be tested. The observation optical system 1 generally comprises a lens 3, an aiming plate 4 as observation means, and an ocular lens 5, so that an image of the anterior portion of the eye to be tested can be enlarged for observation by the ocular lens 5. Disposed at a focal position of the lens 3 is a fixation light source 6. A person to be tested sees this fixation light source 6 at an indefinite distance through the lens 3 while being tested. The observation optical system 1 is provided at a co-axis of its optical axis l with a fluid ejection nozzle 7. The fluid ejection nozzle 7 ejects an air pulse as a fluid for transfiguring the cornea from a front end 7a of the nozzle 7 toward the cornea 2 to be tested. The cornea 2 is flattened under pressure in an applanation state as shown in FIG. 3 by the air pulse.

The air pulse is ejected when a corneal axial line m connecting a corneal curvature center $O_1$ to a corneal vertex $O_2$ is in alignment with the optical axis l, and a distance $l_1$ from the corneal vertex $O_2$ to the nozzle front end 7a is set in a predetermined distance. The non-contact type tonometer has an alignment adjustment apparatus for adjusting the position from the nozzle front end 7a to the corneal vertex $O_2$. The alignment apparatus comprises a first alignment optical system 8, and a second alignment optical system 9. The pair of alignment optical systems 8 and 9 intersect at one point at the respective optical axes thereof that point is located on the optical axis l of the observation optical system. Due to the foregoing, both the alignment optical systems 8 and 9 are disposed symmetrically with relative to each other about the optical axis l.

A first index projection system 8a of the first alignment optical system 8 comprises an index light source 10, a lens 11, a diaphragm 12, a half mirror 13, a variable diaphragm 14, and a lens 15. A second index projection system 9a of the second alignment optical system 9 generally comprises an index light source 16, a lens 17, a diaphragm 18, a half mirror 19, and a lens 20.

The index spot light from the index light source 10 is formed with an image within a plane including the diaphragm by the lens 11, guided to the lens 15 as if it was produced from the diaphragm 12, and converted to a bundle of parallel rays for projecting toward the cornea 2 by the lens 15. On the other hand, the spot light from the index light source 16 is formed with an image within a plane including the diaphragm 18 by the lens 17, guided to the lens 20 as if it was produced from the diaphragm 18, and converted to a bundle of parallel rays for projecting toward the cornea by the lens 20.

The cornea 2 is formed with virtual images i1 and i2 of an index spot light by the specular reflection thereof. These virtual images i1 and i2 are formed in symmetric positions with the optical axis l serving as a line of symmetry when a corneal axis line m and the optical axis l are in alignment with each other.

Figure 4:
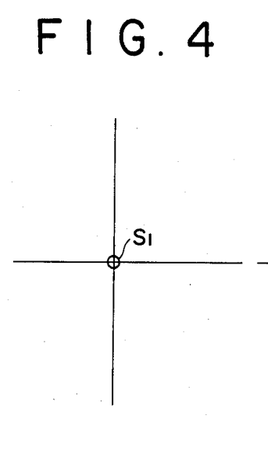
FIGS. 4 through 6 are illustrations for explaining the operation of a non-contact type tonometer according to the present invention at a time when an alignment is adjusted.
Figure 5:
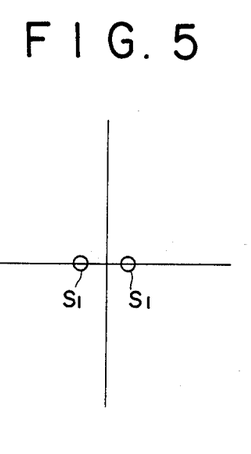
Figure 6:
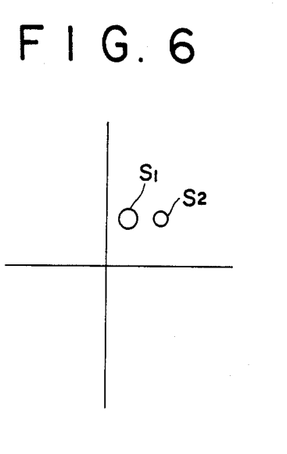

The first alignment optical system 8 has, as shown in FIG. 2, a first index detection system 8b for guiding reflection light for forming the virtual image 12 on the aiming plate 4 through a half mirror 13, total reflection mirrors 21, 22 and 23, and half mirrors 24 and 25. Similarly, the second alignment optical system 9 has a second index detection system 9b for guiding reflection light for forming the virtual image i1 on the aiming plate 4 through half mirrors 19, 26, a total reflection mirror 27, and half mirrors 28, 24, and 25. The aiming plate 4 is formed with a pair of index images S1 corresponding to the index spot light. The pair of index images S1 are, as shown in FIG. 4, superposed at an intersecting point of a cross line of the aiming plate 4, when the optical axis l and the corneal axial line m are in alignment with each other, and a distance l1 from a nozzle front end 7a to a corneal vertex $O_2$ is set to a predetermined distance d. When the optical axis l and the corneal axial line m are not in alignment with each other, or the distance l1 from the nozzle front end 7a to the corneal vertex $O_2$ is not set to the predetermined distance, as shown in FIGS. 5 and 6, the pair of index images S1 are visually separated, and the same time, the pair of index images S1 are blurred. Accordingly, alignment can be confirmed by the superposed relation of the pair of index images S1, and the alignment thereof at the intersecting point of the cross line.

In this embodiment, there are disposed liquid crystal shutters 29 and 30 (FIG. 2) as douser plates in the middle of the optical system paths for guiding the reflection light for forming the virtual images i1 and i2 based on the corneal specular reflection to the aiming plate 4. The liquid crystal shutters 29 and 30 are electrically controlled, so that when one of the liquid crystal shutters 29 and 30 is in its doused state, the other is in a non-doused state. When the pair of index images S1 are not in superposed relation, the blinking of the index images S1 can be visually confirmed. Accordingly, whether the pair of index images S1 are in superposed relation can also be confirmed by confirming the blinking of the pair of index images S1.

The half mirror 25 has the function that a part of the reflection light for forming the virtual images i1 and i2 based on the corneal specular reflection is guided to a detector 32 (FIG. 2) through a diaphragm 31. The detector 32 detects a maximum level of light when the corneal axial line m1 and the optical axis 1 are in alignment and the distance d from the corneal vertex O2 to the nozzle front end 7a is set to the predetermined distance. When these conditions occur a drive signal is outputted toward an air pulse generator (not shown). Actuation of the air pulse generator causes the air pulse to be ejected from the fluid ejection nozzle 7. In FIG. 3, an arrow X shows the ejection direction of the air pulse.

The first alignment optical system 8 serves as a detection light projection optical system for projecting a corneal transfiguration detection light when the cornea is transfigured. A part of the second alignment optical system constitutes a part of the light receiving optical system for receiving the reflection light of the corneal transfiguration detection light. The index spot light from the index light source 10 is guided to the half mirror 13 as a corneal transfiguration detection light, passed through a variable diaphragm 14 and guided to a lens 15. As a result, a bundle of parallel rays is projected toward the cornea 2 and reflected by the cornea 2. The reflection light is guided to a diaphragm 33 through lens 20, half mirror 19, and half mirror 26, and formed as an image at the diaphragm 33, as detected by a detector 34. Due to the foregoing, the applanation state of the cornea 2 is electrically detected.

Figure 7:
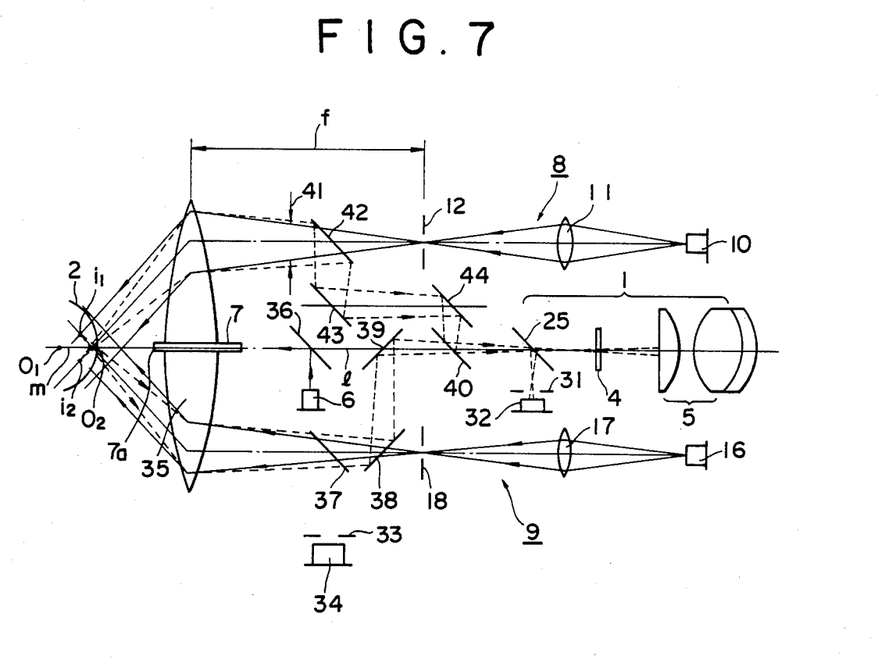
FIG. 7 is an optical system diagram of a reflection light flux at a time when the alignment thereof is adjusted.
Figure 8:
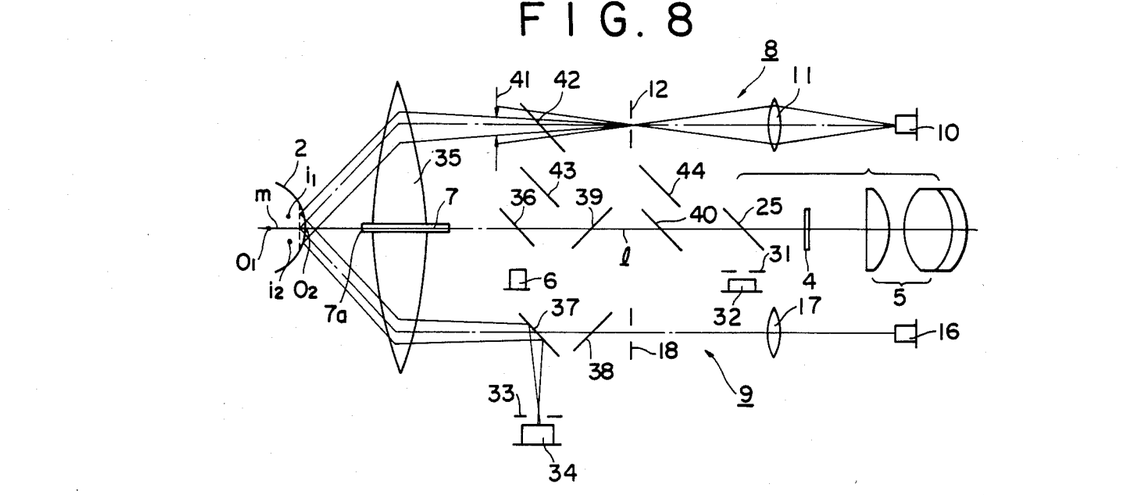
FIG. 8 is an optical system diagram for explaining a detection optical path thereof at a time when a cornea is transfigured.

FIGS. 7 and 8 illustrate a non-contact type tonometer according to a second embodiment of the present invention, in which an objective lens 35 is used both for the lens 15 of the first alignment optical system 8 and the lens 20 of the second alignment optical system 9 in the aforementioned first embodiment. The diaphragms 12 and 18 are each disposed at a position of a focus f of the objective lens 35, so that a pair of spot lights are converted to corresponding bundles of parallel rays by the objective lens 35 and are projected to the cornea 2. The reflection light for forming the virtual image 12 based on the corneal specular reflection is guided to the aiming plate 4 through objective lens 35, variable diaphragm 41, half mirror 42, total reflection mirrors 43 and 44, half mirror 40, and half mirror 25, and are formed as an image on the aiming plate 4. A part of the reflection light is guided to the detector 32 by the half mirror 25, as shown in FIG. 7.

Similarly, the reflection light for forming a virtual image i1 based on the corneal specular reflection is guided to the aiming plate 4 through the objective lens 35, half mirrors 37, 38, 39, 40, and 25 and formed as an image thereon. At the same time, a part of the reflection light is guided to the detector 32 by the half mirror 25.

In this embodiment, the first alignment optical system 8 serves as a detection light projection optical system for projecting a corneal transfiguration detection light when the cornea is transfigured, and a part of the second alignment optical system 9 serves as a light receiving optical system for receiving a part of the corneal transfiguration detection light. As shown in FIG. 8, the index spot light is passed through the variable diaphragm 41, guided to the objective lens 35, converted to a bundle of parallel rays by the objective lens 35, reflected by the cornea 2 in its applanation state, and guided to the detector 34 through the objective lens 35 and the half mirror 37.

According to a second embodiment of the invention, the objective lens 35 can be used for both of the index spot light projection optical systems 8 and 9. Accordingly, the first and the second alignment optical systems 8 and 9 can be more compact than those of the first embodiment. In FIGS. 7 and 8, reference numeral 36 denotes a half mirror for guiding a fixation sight index light from the fixation sight light source 6 to the eye to be tested. In the above-mentioned respective embodiments, the nozzle tube 7 and the optical axis 1 of the observation optical system are in alignment with each other. However, the present invention is not necessarily limited to these embodiments.

Next, a non-contact type tonometer according to a third embodiment of the present invention will be described with reference to FIGS. 9 through 18.

The observation optical system 1 includes an illuminating means 50 for illuminating the anterior portion of the eye under test, an objective lens 51 for forming an image of the anterior portion, and an observing means 52 for observing the image. The illuminating means 50 comprises four green light emitting diodes 50a–50d. The green light emitting diodes 50a–50d are arranged around the optical axis 1 at equal angles. An image pickup tube 53 is used as the observing means 52 in this embodiment, and the image of the anterior portion of the eye to be tested is formed on the sensing surface 53a of the image pick-up tube 53 through the objective lens 51. Also, a reticle image is formed on the sensing surface 53a through a reticle image projection optical system as will be described later.

Figure 10:
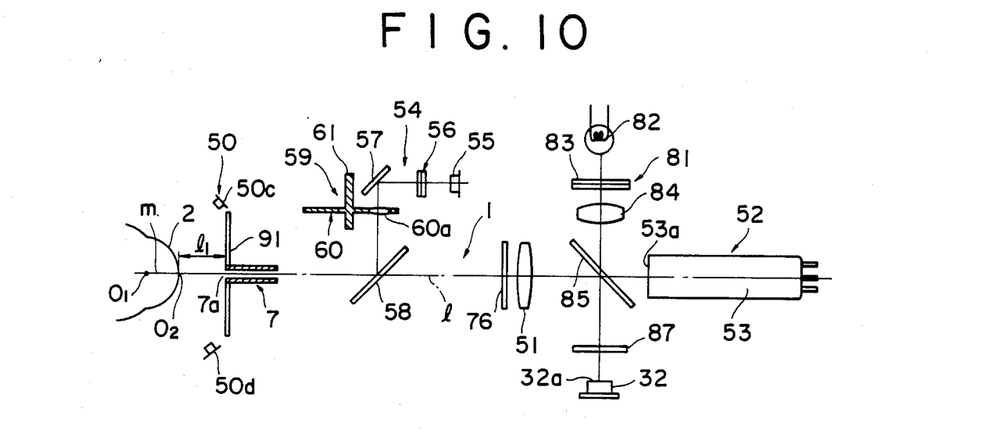
FIG. 10 is an optical system diagram for explaining a reticle image projection optical system and a diopter compensation optical system of a non-contact type tonometer.
Figure 13:
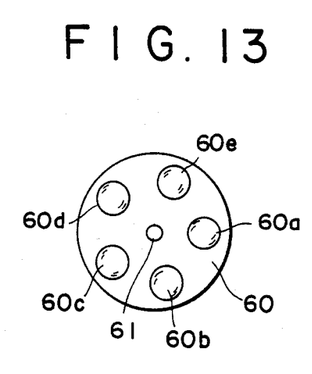
FIG. 13 is an illustration for explaining the diopter compensation optical system shown in FIG. 10.

In FIG. 10, reference numeral 54 denotes a fixation sight mark projection optical system. The fixation mark projection optical system 54 includes a green light emitting diode 55 as a fixation sight light source, a fixation sight mark plate 56, a total reflection mirror 57, and a half mirror 58. A diopter compensation optical system 59 is disposed between the total reflection mirror 57 and the half reflection mirror 58. The diopter compensation optical system 59 comprises a group of lenses mounted on a turret plate 60, as shown in FIG. 13. The turret plate 60 is fixed with diopter compensation lenses 60a–60e arranged around a rotary shaft 61 of the turret plate 60. In this embodiment, the lens 60a is for 0 diopter. Likewise, the lens 60b is for −3 diopter, lens 60c for −10 diopter, lens 60d for +10 diopter and lens 60e for +3 diopter. The rotation of the turret plate 60 causes the lenses 60a–60e to be selectively added to the fixation mark projection optical system 54 so that diopter of the eye under test may be compensated.

In this embodiment, the first alignment optical system 8 comprises an infrared light emitting diode 62 serving as an index spot light forming means, an index projection optical system 63 adapted to project the infrared light serving as the index spot light in the form of a bundle of parallel rays toward the cornea 2, and an index detection system 64 adapted to introduce a virtual image of the index spot light produced by means of the corneal specular reflection of the eye under test 2 to a sensing surface 53a through an index projection optical system (as will be described later) of the other alignment optical system 9.

The second alignment optical system 9 comprises an infrared light emitting diode 65 serving as an index spot light forming means, an index projection optical system 66 adapted to project the infrared light serving as the index spot light in the form of a bundle of parallel rays toward the cornea 2, and an index detection system 67 adapted to guide a virtual image of the index spot light produced by means of the corneal specular reflection of the eye 2 under test to the sensing surface 53a through an index projection optical system 63 of the other alignment optical system 8. The index projection optical system 63 generally comprises a band-pass filter 68, a lens 69, a half mirror 70 and an objective lens 71. While, the index projection optical system 66 generally comprises a band-pass filter 72, a lens 73, a half mirror 74, and an objective lens 75.

The infrared light emitting diode 62 and the infrared light emitting diode 65 emit infrared light having different wavelengths with respect to each other. In this embodiment, the wavelength of the light emitted by the infrared light emitting diode 62 is in the vicinity of 760 nm at its central wavelength, while the wavelength of the light emitted by the other infrared light emitting diode 65 is in the vicinity of 830 nm at its central wavelength. The band-pass filter 68 transmits the infrared light of the wavelength bands as indicated by character C in FIG. 14. On the other hand, the other band-pass filter 72 transmits the infrared light in the wavelength band as indicated by character D in FIG. 14.

Figure 14:
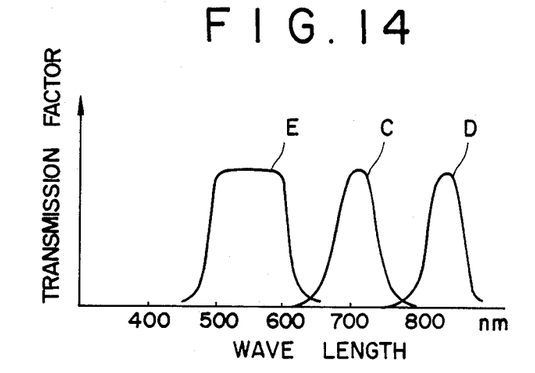
FIG. 14 is an illustration for explaining a character of a filter according to the present invention.

In FIG. 14, reference character E denotes a transmittance characteristic of a band-pass filer 76. The band-pass filter 76 is disposed between the objective lens 51 and the half mirror 58 of the observation optical system 1 to cut the infrared light and permit the green light reflected on the anterior portion of the eye under test to transmit therethrough. The band-pass filter 68 and band-pass filter 72 are formed with diaphragms 68a, 72a by means of vacuum evaporation coating film, respectively. The infrared light emitted from the infrared light emitting diode 62 and the infrared light emitted from the other infrared light emitting diode 65 are transmitted through the diaphragms 68a, 72a and introduced to the lenses 69, 73, respectively.

Figure 9:
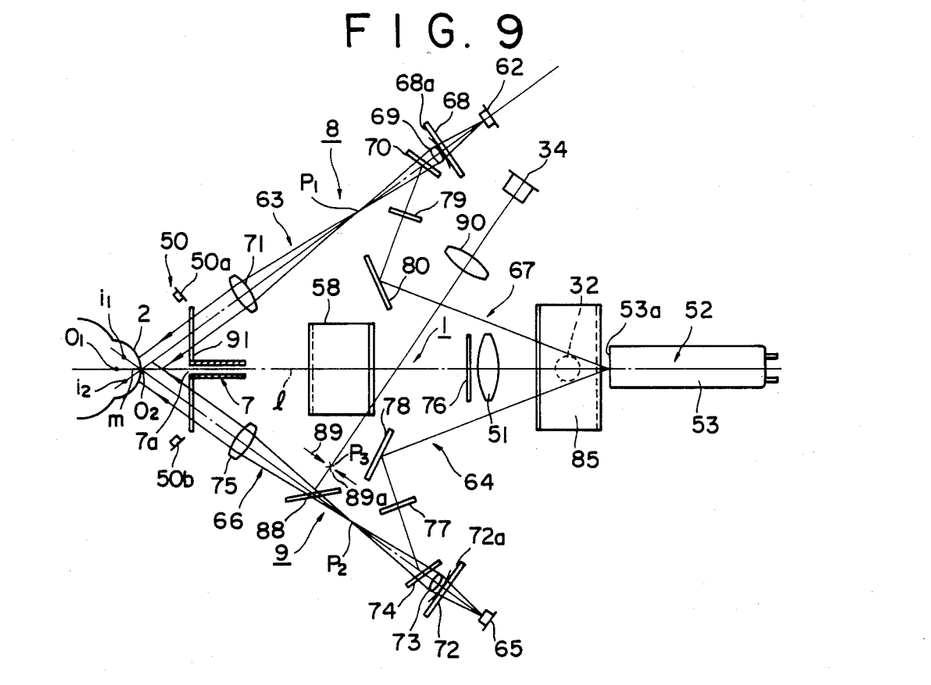
FIG. 9 is an optical system diagram showing a constitution of an important portion thereof.

The lenses 69 and 73 form intermediate images $P_1$, $P_2$ from the respective infrared light sources. The objective lenses 71, 75 are positioned such that their respective focal points are coincident with the positions where the intermediate images $P_1$, $P_2$ are formed, and convert the infrared lights formed as the intermediate images $P_1$, $P_2$ into bundles of parallel rays. As shown in FIG. 9, since the cornea 2 is formed with virtual images $i_1$, $i_2$ of the index spot light by the corneal specular reflection based on the projection of the bundle of parallel rays, when the corneal axial line m and optical axis 1 are brought into alignment with each other, the symmetrical positions are formed, with the corneal axial line m serving as an axis of symmetry.

Figure 12:
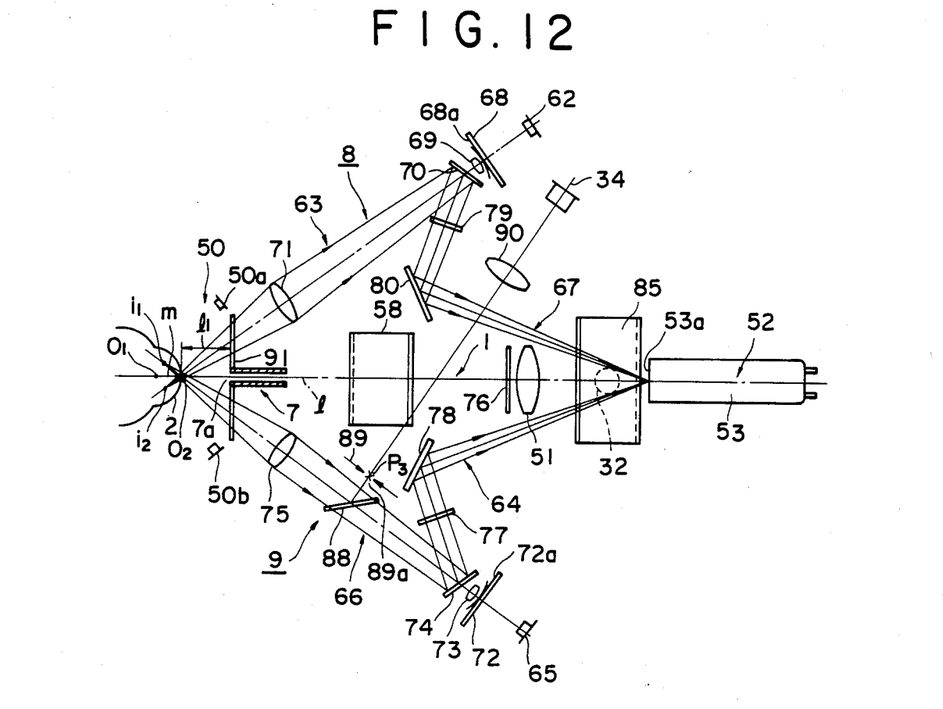
FIG. 12 is an optical system for explaining a reflection light flux.

The virtual image $i_1$ is formed by projection of the index spot light of the first alignment optical system 8, while the virtual image $i_2$ is formed by projection of the index spot light of the second alignment optical system 9. As shown in FIG. 12, the index projection optical system 63 introduces the reflection light which forms the virtual image $i_2$ to the index detection system 67 through the half mirror 70. The other index projection optical system 66 introduces the reflection light which forms the virtual image $i_1$ to the index detection system 64 through the half mirror 74. The index detection system 64 comprises a filter 77, and a total reflection mirror 78. While, the index detection system 67 comprises a filter 79 and a total reflection mirror 80.

A filter 79 cuts the infrared light having its central wavelength of 760 nm and permits the infrared light having its central wavelength of 830 nm to transmit therethrough. On the other hand, a filter 77 cuts the infrared light having its central wavelength of 830 nm and permits the infrared light having its central wavelength of 760 nm to transmit therethrough. The reflection light for forming the virtual images $i_1$, $i_2$ are introduced to the sensing surface 53a of the image pick-up tube 53 as observation means by index detection systems 64, 67, and are formed as a pair of index images $S_1$ thereon. A reticle image projection optical system 81 will be described next.

Figure 15:
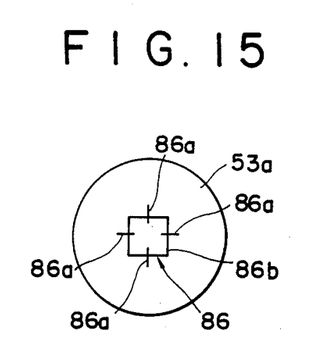
FIGS. 15-18 are schematic illustrations of reticle images formed in an image pick up plane by the reticle image projection optical system shown in FIG. 10.

The reticle image projection optical system 81 comprises an illumination light source 82, a reticle plate 83, a projection lens 84, and a half mirror 85. A reticle image 86 is, as shown in FIG. 15, formed on the sensing surface 53a of the image pick-up tube 53 by the reticle image projection system 81. In this FIG. 15, 86a denotes a cross line, 86b denotes a boundary frame adapted to determine the completion of alignment. When the pair of index images $S_1$ are within the boundary frame 86b, an air pulse generator (not shown) is driven by a detector as will be described later, and an air pulse is ejected from the nozzle tip end 7a.

The half mirror 85 reflects a part of the corneal specular reflection light to the detector 32. The detector 32 is arranged in an optical conjugate position with the image sensing surface 53a of the image pick-up tube 53. A filter 87 is provided between the half mirror 85 and the detector 32 in order to cut the illumination light of the illumination light sources 82 and 50a–50d and permit the infrared light to transmit therethrough and to reflect thereon. Because of the foregoing arrangement, the detector 32 can receive only the corneal specular reflection light without getting influence of the illumination light emitted from the illumination light source 82.

Figure 16:
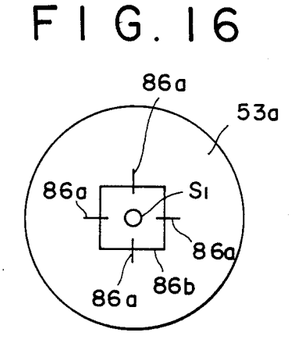
Figure 17:
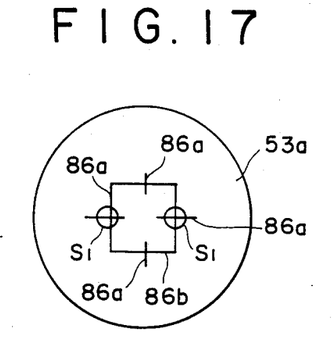
Figure 18:
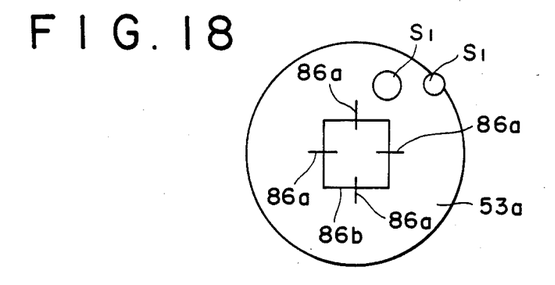

When the optical axis 1 and the corneal axial line m are in alignment with respect to each other and the distance $l_1$ from the nozzle tip end 7a to the corneal vertex $O_2$ is set to be in the predetermined distance, the pair of index images $S_1$ are, as shown in FIG. 16, caused to be in a superposed relation with respect to each other at the intersecting point of the cross line 86a of the reticle plate and simultaneously the images become sharp. On the contrary, when the optical axis 1 and the corneal axial line m are not in alignment with respect to each other, or when distance from the nozzle tip end 7a to the corneal vertex $O_2$ is not set to be in the predetermined distance, the pair of index images $S_1$ are separated, as shown in FIGS. 17 and 18, and simultaneously the pair of index images $S_1$ are blurred. Accordingly, the alignment can be controlled in such a manner as to confirm the mutual superposition of the index images $S_1$ and the alignment of the images with the intersecting point of the cross line 86a through the image pick-up tube 53.

Figure 11:
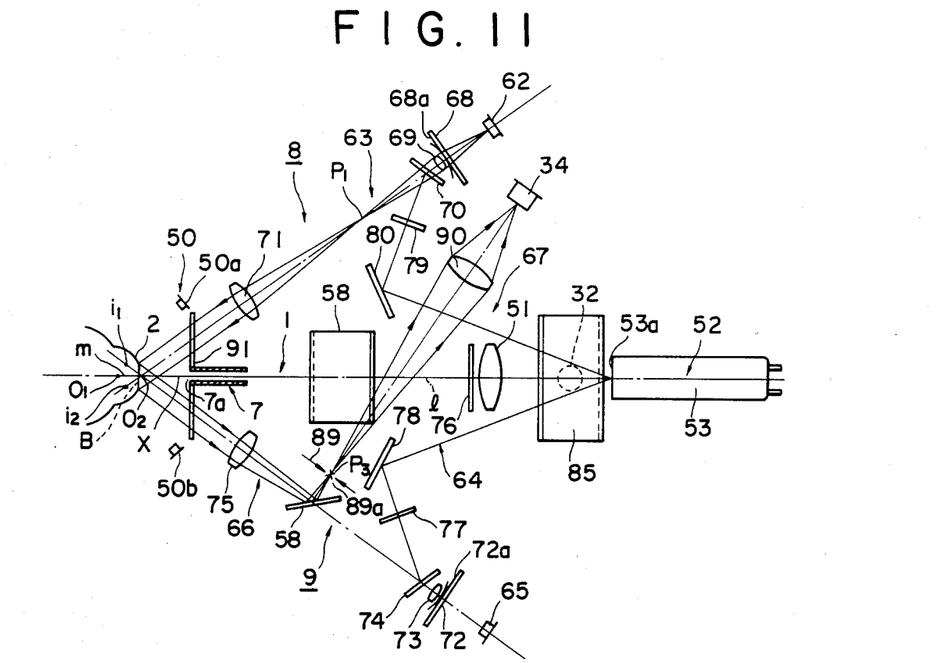
FIG. 11 is an optical system for explaining a corneal transfiguration detecting condition.

The first alignment optical system 8 serves as a projection optical system of a corneal transfiguration monitoring system for projecting the corneal transfiguration detecting light onto the cornea at the time when the cornea 2 is transfigured. A part of the second alignment optical system 9 constitutes a part of the receiving optical system of the corneal transfiguration monitoring system for receiving the reflection light of the corneal transfiguration detection light. The index spot light emitted from the infrared light emitting diode 62 is, as shown in FIG. 11, introduced to the diaphragm 68a as the corneal transfiguration detection light, then introduced to the lens 69 through the diaphragm 68a, and formed as an intermediate image $P_1$ by the lens 69. The width of the optical flux of the infrared light serving as the corneal transfiguration detection light is identical with that of the optical flux of the infrared light serving as the index spot light in this embodiment. The intermediate image $P_1$ is converted to a bundle of parallel rays by the objective lens 71 and projected to the cornea 2.

The corneal transfiguration detection light is, as shown in FIG. 11, reflected on the cornea 2 and introduced to the objective lens 75. A half mirror 58 constituting a part of the receiving optical system is disposed between the objective lens 75 and the half mirror 74. The half mirror 74 reflects the corneal transfiguration detection light toward the diaphragm 89. The diaphragm 89 constitutes a part of the receiving optical system. The diaphragm 89 is arranged in a conjugate position with respect to the focal position of the objective lens 75. The corneal transfiguration detection light is formed as an intermediate image $P_3$ in the position where the diaphragm 89 is located by the objective lens 75. The size of the intermediate image $P_3$ is identical with that of an opening 89a formed in the diaphragm 89. The intermediate image $P_3$ is formed on a detector 34 through a relay lens 90. Based on the foregoing, the degree of corneal flatness under pressure is electrically detectable from the changes of the reflected optical quantity of the cornea 2. In the figure, 91 denotes a dust-proofing glass plate.

In this embodiment, the filter 79 cuts the reflected infrared light which forms the virtual image $i_1$ and permits only the reflected infrared light which forms the virtual image $i_2$ to transmit therethrough. The filter 77 cuts the reflected infrared light which forms the virtual image $i_2$ and permits only the reflected infrared light which forms the virtual image $i_1$ to transmit therethrough. This means that reflection light reflected on the anterior portion of the eye to be tested, such as the cornea, iris, and crystalline lens, and returned to the index projection optical systems 63, 66, which are adapted to project the index spot light for forming the virtual images $i_1$, $i_2$ among the corneal specular reflection light which forms the virtual images $i_1$, $i_2$, can be cut. Accordingly, deterioration of the index images $S_1$ formed on the sensing surface 53a of the image pick-up tube 53 and the receiving surface 32a of the detector 32 can be prevented.

Figure 19:
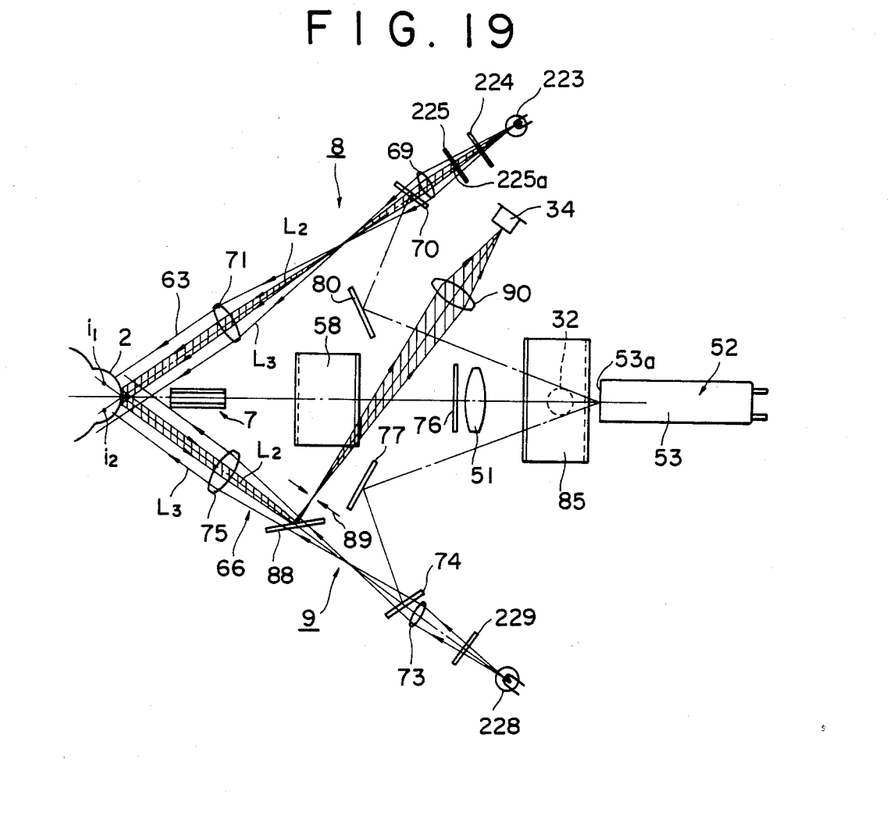
FIG. 19 is an illustration showing an important portion of an optical system thereof.

Next, a non-contact type tonometer according to a fourth embodiment of the present invention will be described with reference to FIG. 19.

In the non-contact type tonometer according to the fourth embodiment, an index spot light for alignment and a corneal transfiguration detection light are different in wavelengths with respect to each other. An index projection optical system 63 includes an index spot light generation means, and corneal transfiguration detection light generation means. The index spot light generation means and the corneal transfiguration detection light generation means generally comprise an incandescent lamp 223 as a common illumination light source, a high-pass filter 224, and a wavelength selection filter 225.

Figure 20:
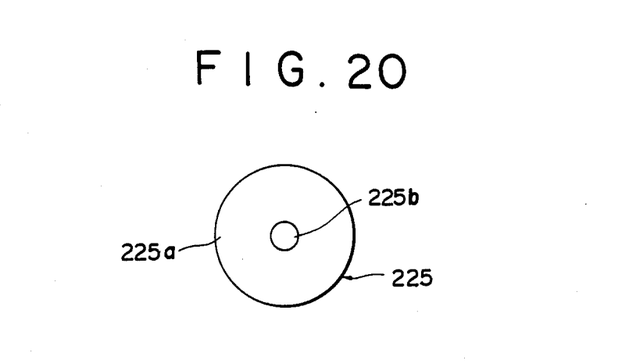
FIG. 20 is a plan view of a wave length selection filter shown in FIG. 19.

The high-pass filter 224 transmits illumination light having a wavelength of more than 600 nm among illumination light emitted from the incandescent lamp 223. The wavelength selection filter 225, as shown in FIG. 20, transmits illumination light having a wavelength of more than 700 nm among illumination light emitted from the incandescent lamp 223 at the peripheral portion 225a thereof, and illumination light having a wavelength of more than 600 nm at the central portion 225b.

Figure 21:
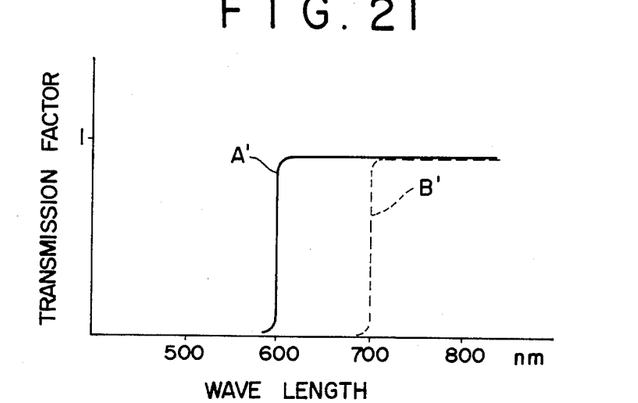
FIG. 21 is a transmission characteristic graph of the wave length selection filter shown in FIG. 19.
Figure 22:
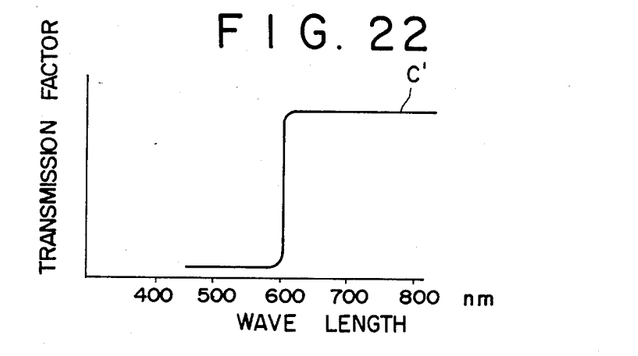
FIG. 22 is a transmission characteristic graph of the wave length selection filter shown in FIG. 19.
Figure 23:
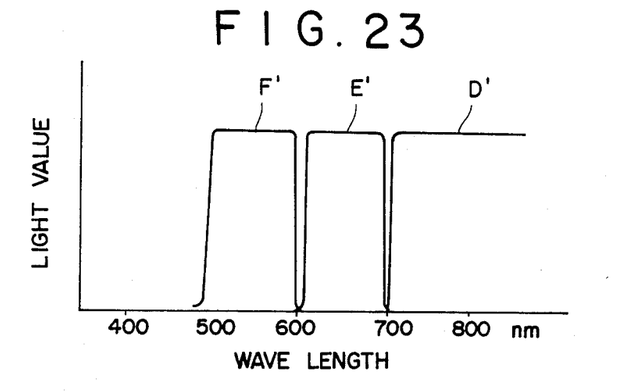
FIG. 23 is an illustration for showing a relation of a wave length area among a front eye portion illumination light, an index spot light, and a corneal transfiguration detection light of a non-contact type tonometer according to the present invention.

FIG. 21 illustrates a characteristic of this wavelength selection filter 225, wherein reference character A' denotes a filter characteristic at a central portion 225a, while reference character B' denotes a filter characteristic at a peripheral portion 225b. In FIG. 22, reference character C' denotes a filter characteristic of a high-pass filter 224. Illumination light emitted by the incandescent lamp 223 passes through the high-pass filter 224 and the wavelength selection filter 225 and becomes corneal transfiguration detection light L2 (light flux shown by hatching in FIG. 19) and an index spot light L3. In this embodiment, an illumination light having a wavelength range of from 600 nm to 700 nm is used as the corneal transfiguration detection light L2 as shown by reference character E' in FIG. 23, and an illumination light having a wavelength range of more than 700 nm as an index spot light L3 as shown by reference character D' in FIG. 22. In FIG. 23, reference character F' denotes a transmission wavelength characteristic of a band pass filter 76 as in the above-mentioned third embodiment.

An index projection optical system 66 comprises an incandescent lamp 228 as an illumination light source, a high-pass filter 229, a visible light reflection mirror 88, a half mirror 229, a visible light reflection mirror 88, a half mirror 74, and an objective lens 75 for alignment/applanation detection. The high-pass filter 229 cuts illumination light having a wavelength range of less than 600 nm among illumination light ejected from the incandescent lamp 228, and transmits illumination light having a wavelength range of more than 600 nm. The visible light reflection mirror 88 reflects the illumination light having a wavelength range of less than 700 nm and transmits light of more than 700 nm in wavelength. The illumination light emitted by the incandescent lamp 228 becomes an index spot light L3 having a wavelength range of more than 700 nm at a time when it passes through the high-pass filter 229 and the visible light reflection mirror 88.

As described in the foregoing, according to the present invention, there is provided a pair of alignment optical systems in symmetric positions with respect to an optical axis of an observation optical system for projecting a pair of index spot lights toward a cornea after converting it to a bundle of parallel rays and for forming a virtual image of a pair of index spot lights due to corneal specular reflection in symmetric positions relative to the optical axis of the observation optical system when a corneal axial line and the optical axis of the observation optical system are in alignment with each other. Further, the pair of alignment optical systems are constituted such that a reflection light of an index spot light emitted by one of the alignment optical systems and adapted to form a virtual image based on a corneal specular reflection is formed as an index image on an aiming plate through the other alignment optical system. Accordingly, when the optical axis of the observation optical system and the corneal axial line connecting the corneal vertex to the corneal curvature center are not in alignment relative to each other, and the distance from the corneal vertex to the ejection nozzle front end is not set to a predetermined distance, a pair of index images corresponding to virtual images based on the corneal specular reflection are visually confirmed in a separated and blurred state. Thus, by confirming the superposed relation to the pair of the index images formed on the aiming plate, alignment between the optical axis of the observation optical system and the corneal axial line, and the distance from the fluid ejection nozzle front end to the corneal vertex can be adjusted simultaneously. Thus, alignment adjustment can be accurately. Furthermore, since alignment is made in such a manner as to bring the corneal vertex under test in alignment with a point where the optical axes of the first and second alignment optical systems of the optical axis of the observation optical system intersect, the present invention has such an advantage as that the work distance does not depend on the radius of curvature of the cornea under test.

What is claimed is:

1. A non-contact type tonometer for measuring intraocular pressure of a human eye, comprising:
    a fluid ejection nozzle having a central axis and adapted to eject a fluid toward the cornea of an eye under test for transfiguring the cornea;
    an alignment control means having observation means and including first and second alignment optical systems having corresponding optical axes disposed in such a manner as to intersect at one point on the central axis of said fluid ejection nozzle and being symmetrically disposed about the central axis of said fluid ejection nozzle;
    said first and second alignment optical systems each including a corresponding index projection optical system adapted to project an associated index spot light toward the cornea and a corresponding index detection system adapted to form a virtual image of said associated index spot light on said observation means as an index image by means of corneal specular reflection from the eye under test through a part of said index projection optical system of the other alignment control system
    whereby alignment of the eye under test and said fluid ejection nozzle is indicated by a superposed relation of the pair of index images formed on said observation means.

2. The non-contact type tonometer according to claim 1, wherein said first alignment optical system is used as a detecting light projection optical system adapted to project a corneal transfiguration detecting light at a time when said fluid is ejected from said fluid ejection nozzle, and the second alignment optical system constitutes a part of a receiving optical system adapted to receive the reflected light of said corneal transfiguration detecting light.

3. The non-contact type tonometer according to claim 1, wherein each of said first and second alignment optical systems is provided with a corresponding light douser disposed in an optical path for introducing the reflection light reflected from the cornea to said observation means and being adapted to be activated when the douser corresponding to the other alignment optical system is not activated such that the pair of index images appear to blink when said index images are not in a superposed relation.

4. The non-contact type tonometer according to claim 1, wherein said observation means is provided with an illumination means for illuminating an anterior portion of the eye under test, and an objective lens for forming an image of said anterior portion of the eye under test as as intermediate image, said pair of index spot lights being infrared light having different wave lengths and the illumination light of said illumination means being visible light.

5. The non-contact type tonometer according to claim 1, wherein said observation means is provided with an illumination light generation means for illuminating the anterior portion of the eye under test and an object lens for forming an image of said anterior portion thereof as an intermediate image, said first alignment optical system having a corneal transfiguration detection light generation means for generating a corneal transfiguration detection light and having a detecting light projection optical system for projecting said corneal transfiguration detection light, said second alignment optical system having a receiving means for receiving the reflection light of said corneal transfiguration detection light based on said corneal transfiguration, and wherein the illumination light of said illumination generation mean, said index spot light, and said corneal transfiguration detection light are different in wave length range.

6. The non-contact type tonometer according to claim 5, wherein the wave length of the illumination light is in the range of 500 to 600 nm, the wave length of said index spot light is more than 700 nm, and the wave length of said corneal transfiguration detection light is in the range of 600 to 700 nm.

7. The non-contact type tonometer according to claim 6, wherein said index spot light generation means and said corneal transfiguration detection light generation means in said first alignment optical system comprises a common illumination light source, a wave length selective filter for selectively transmitting a first illumination light flux having a wave length of more than 700 nm out of the illumination light from the peripheral portion of said common illumination light source, and for selectively transmitting a second illumination light flux having a wave length of more than 600 nm out of the illumination light from the central portion of said common illumination light source, and wherein said second alignment optical system includes visible light reflection means for reflecting light emitted by said wavelength selective filter having a wave length of 600 to 700 nm and for transmitting light emitted from said wavelength selective filter which has a wave length greater than 700 nm.

8. A non-conductive type tonometer comprising:
    a fluid ejection nozzle having a central axis and adapted to eject a fluid toward the cornea of an eye to be tested for deforming the cornea;
    an alignment control means having observation means, a first alignment optical system, and a second alignment optical system;
    said first alignment optical system including a first index projection system and a first index detection system having a first partial common optical axis therewith;
    said second alignment optical system including a second index projection system and a second index detection system having a second partial common optical axis therewith;
    said first and second partial common optical axes intersecting each other at one point on said central axis of said fluid ejection nozzle and being obliquely disposed symmetrically with respect to said axis of said fluid ejection nozzle;

said first index projection system including a first index light source and a first projection lens for projecting first index light rays from said first index light source toward the cornea in parallel with said first partial common optical axis;

said second index projection system including a second index light source and a second projection lens for projecting second index light rays from said second index light source toward the cornea in parallel with said second partial common optical axis, said first index light rays being reflected by the cornea to transmit a first virtual index image along said second partial common optical axis, and said second index light rays being reflected by the cornea to transmit a second virtual index image along said first partial common optical axis;

first index projection lens of said first index detection system adapted to form said second virtual index image on said observation means as a first alignment index image; and said second index projection lens of said second index detection system adapted to form said first virtual index image on said observation means as a second alignment index image, whereby a desired alignment condition and a desired working distance are established when said first and second virtual index images are transmitted along said second and first partial common axes, respectively to cause said first and second alignment index images to be superposed and to coincide with a predetermined position in an observation view field of said observation means.

9. The non-contact type tonometer according to claim 8, wherein said first alignment optical system includes a detecting light projection optical system adapted to project a corneal deformation detecting light coincident with the system of the fluid from said fluid ejection nozzle, and said second alignment optical system includes a receiving optical system adapted to receive said corneal deformation detecting light reflected by the cornea.

10. The non-contact type tonometer according to claim 9, wherein said first and second index light rays and said corneal deformation detection light are different in wave length.

11. The non-contact type tonometer according to claim 8, wherein each of said first and second alignment optical system includes a light douser adapted to be alternatively activated to alternately douse said first and second alignment index images such that said first and second alignment index images blink when the desired alignment condition and the desired working distance are not established.

12. The non-contact type tonometer according to claim 8, wherein said observation means includes an illumination light source for illuminating an anterior portion of the eye to be tested and an objective lens for forming an image of the anterior portion of the eye.

13. The non-contact type tonometer according to claim 12, wherein said first and second index light rays are infrared light rays having different wave lengths, and said illumination light radiated from said illuminatin light source is visible light.

14. The non-contact type tonometer according to claim 12, wherein said first and second index light rays, said corneal deformation detecting light, and said illumination light are different in wave length.

15. The non-contact type tonometer according to claim 14, wherein said illumination light has a wave length in the range of 500 and 600 nm, said first and second index light rays have wave lengths greater than 700 nm, and said corneal deformation detecting light has a wave length in range of 600 and 700 nm.

16. The non-contact type tonometer according to claim 15 wherein said first alignment optical system further comprises a common light source, and a wave length selective filter for selectively transmitting said first index light rays from said common light source at the peripheral portion thereof and for selectively transmitting a light flux having a wave length greater than 600 nm from said common light source at the central portion thereof, and wherein said second alignment optical system further comrises a visible light reflection means for selectively reflecting a visible light flux having a wave length in the range of 600 nm to 700 nm and for selectively transmitting said first index light rays so that the visible light flux is used as said corneal deformation detection light.

* * * * *